United States Patent
Lee

(12)
(10) Patent No.: US 6,537,590 B1
(45) Date of Patent: Mar. 25, 2003

(54) SOLUTION AND THE METHOD OF MAKING THE SAME FOR THE TREATMENT OF OSTEOARTHRITIS

(76) Inventor: Troy J. Lee, 17 Daniel Rd., Asheville, NC (US) 28806

( * ) Notice: Subject to any disclaimer, the term of this patent is extended or adjusted under 35 U.S.C. 154(b) by 0 days.

(21) Appl. No.: 10/077,291

(22) Filed: Feb. 19, 2002

(51) Int. Cl.[7] .............................. A61K 33/08
(52) U.S. Cl. .................. 424/692; 514/825; 514/566
(58) Field of Search .................. 424/692; 514/825, 514/566

(56) References Cited

U.S. PATENT DOCUMENTS

| 4,481,197 | A | * | 11/1984 | Rideout et al. | 514/46 |
|---|---|---|---|---|---|
| 4,968,510 | A | * | 11/1990 | Jensen | 424/630 |
| 5,821,265 | A | * | 10/1998 | Schlesinger et al. | 514/492 |
| 5,824,696 | A | * | 10/1998 | Griswold et al. | 514/303 |
| 5,898,037 | A | * | 4/1999 | Marx | 424/49 |
| 5,910,512 | A | * | 6/1999 | Conant | 514/617 |
| 6,166,039 | A | * | 12/2000 | Yaksh | 514/237.2 |
| 6,190,691 | B1 | * | 2/2001 | Mak | 424/449 |
| 6,248,368 | B1 | * | 6/2001 | Valletta | 424/601 |
| 6,288,026 | B1 | * | 9/2001 | Exner et al. | 424/184.1 |
| 2001/0051166 | A1 | * | 12/2001 | Luo et al. | 424/400 |

* cited by examiner

*Primary Examiner*—James H. Reamer

(57) ABSTRACT

A solution and the method of making the same for the treatment of osteoarthritis for treating symptoms of osteoarthritic conditions. The solution and the method of making the same for the treatment of osteoarthritis includes magnesium oxide; ethylenediaminetetraacetic acid; glycerin; and water, all of which are heated and added in a mixture which, after being cooled, is applied to the affected areas for treatment of the osteoarthritic condition.

9 Claims, 1 Drawing Sheet

SOLUTION AND THE METHOD OF MAKING THE SAME FOR THE TREATMENT OF OSTEOARTHRITIS

BACKGROUND OF THE INVENTION

1. Field of the Invention

The present invention relates to osteoarthritic treatment lotions and more particularly pertains to a new solution and the method of making the same for the treatment of osteoarthritis for treating symptoms of osteoarthritic conditions.

2. Description of the Prior Art

The use of osteoarthritic treatment lotions is known in the prior art. More specifically, osteoarthritic treatment lotions heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,910,512; 6,190,691; 5,824,696; 4,481,197; and 6,166,039.

While these devices fulfill their respective, particular objectives and requirements, the aforementioned patents do not disclose a new solution and the method of making the same for the treatment of osteoarthritis. The prior art describes solutions and medicated products for various ailment treatments.

SUMMARY OF THE INVENTION

The general purpose of the present invention, which will be described subsequently in greater detail, is to provide a new solution and the method of making the same for the treatment of osteoarthritis which has many of the advantages of the osteoarthritic treatment lotions mentioned heretofore and many novel features that result in a new solution and the method of making the same for the treatment of osteoarthritis which is not anticipated, rendered obvious, suggested, or even implied by any of the prior art osteoarthritic treatment lotions, either alone or in any combination thereof. The present invention includes magnesium oxide; ethylenediaminetetraacetic acid; glycerin; and water, all of which are heated and added in a mixture which, after being cooled, is applied to the affected areas for treatment of the osteoarthritic condition. None of the prior art uses the combination of ingredients of the present invention in the treatment of osteoarthritis.

There has thus been outlined, rather broadly, the more important features of the solution and the method of making the same for the treatment of osteoarthritis in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

It is an object of the present invention to provide a new solution and the method of making the same for the treatment of osteoarthritis which has many of the advantages of the osteoarthritic treatment lotions mentioned heretofore and many novel features that result in a new solution and the method of making the same for the treatment of osteoarthritis which is not anticipated, rendered obvious, suggested, or even implied by any of the prior art osteoarthritic treatment lotions, either alone or in any combination thereof.

Still another object of the present invention is to provide a new solution and the method of making the same for the treatment of osteoarthritis for treating symptoms of osteoarthritic conditions.

Still yet another object of the present invention is to provide a new solution and the method of making the same for the treatment of osteoarthritis that be easily and conveniently made and used.

Even still another object of the present invention is to provide a new solution and the method of making the same for the treatment of osteoarthritis that causes no side effects, is non-toxic, and effectively reduces the pain associated with the osteoarthritic condition.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
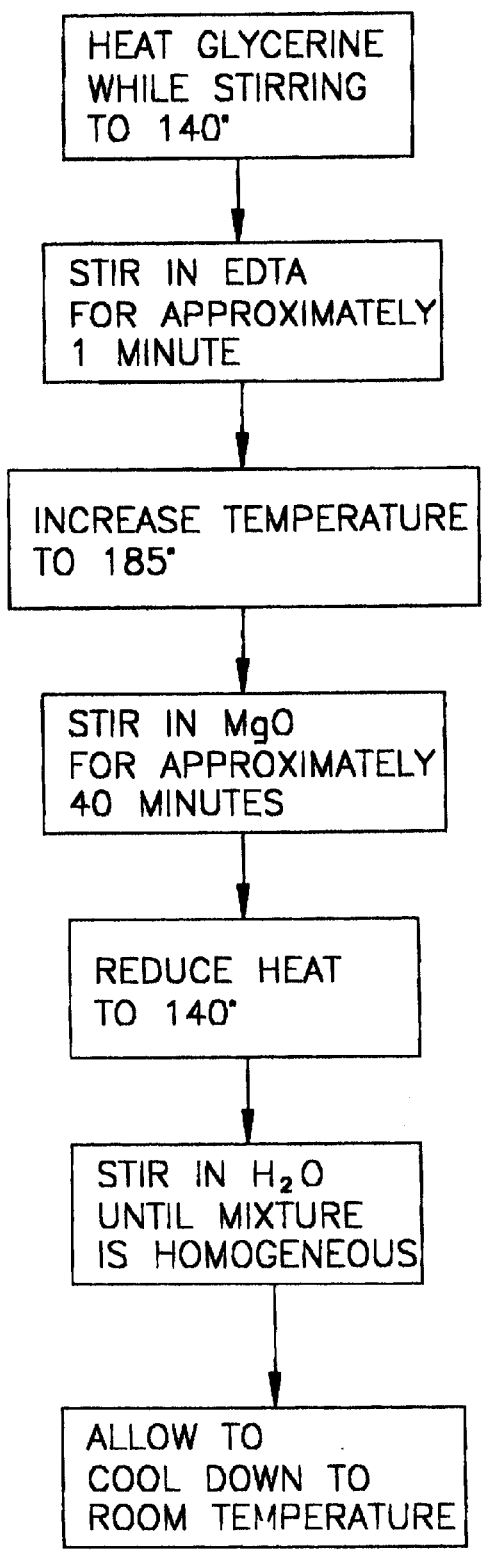
FIG. 1 is a schematic diagram of a new solution and the method of making the same for the treatment of osteoarthritis according to the present invention and shown in use.

With reference now to the drawings, and in particular to FIG. 1 thereof, a new solution and the method of making the same for the treatment of osteoarthritis embodying the principles and concepts of the present invention and generally designated by the reference numeral 10 will be described.

As best illustrated in FIG. 1, the solution and the method of making the same for the treatment of osteoarthritis 10 generally comprises magnesium oxide; ethylenediaminetetraacetic acid; glycerin; and water. Per 100 milliliters, the solution comprises magnesium oxide in an amount of approximately 1 to 2 parts by volume; ethylenediaminetetraacetic acid in an amount of approximately 10 to 20 parts by volume; glycerin in an amount of approximately 70 to 75 parts by volume; and water in an amount of approximately 5 to 15 parts by volume. Preferably, for every 100 milliliters, the solution comprises magnesium oxide in an amount of approximately 1.6 parts by volume; ethylenediaminetetraacetic acid in an amount of approximately 15 parts by volume; glycerin in an amount of approximately 73.4 parts by volume; and water in an amount of approximately 10 parts by volume.

To make the treatment solution, the glycerin is heated to approximately 140 degrees Fahrenheit. Then ethylenediaminetetraacetic acid is added and mixed to the glycerin for approximately 1 minute to form a mixture. The mixture is then heated to approximately 185 degrees Fahrenheit. Upon reaching that temperature, magnesium oxide is added and mixed to the mixture for approximately 40 minutes. After which, the mixture is cooled back to 140 degrees Fahrenheit, and water is then added and mixed in. After further cooling, the mixture is bottled and ready for use.

In use, the treatment solution is applied directly the area of the body such as a joint which has the osteoarthritic condition. The treatment solution is absorbed into the joint with the treatment solution effecting an equilibrium reaction with the calcium ions within the joint. The magnesium oxide would hold the calcium in solution while the ethylenediaminetetraacetic acid would act as a catalyst. The treatment solution would prevent calcium deposits from forming and would decrease existing calcium deposits, and would improve the mobility of the joint.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the solution and the method of making the same for the treatment of osteoarthritis. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. A solution for treating osteoarthritis comprising:

magnesium oxide;

ethylenediaminetetraacetic acid;

glycerin; and water.

2. A solution for treating osteoarthritis as described in claim 1, wherein per 100 milliliters, said solution comprises said magnesium oxide in an amount of approximately 1 to 2 parts by volume; said ethylenediaminetetraacetic acid in an amount of approximately 10 to 20 parts by volume; said glycerin in an amount of approximately 70 to 75 parts by volume; and said water in an amount of approximately 5 to 15 parts by volume.

3. A solution for treating osteoarthritis as described in claim 2, wherein per 100 milliliters, said solution comprises said magnesium oxide in an amount of approximately 1.6 parts by volume; said ethylenediaminetetraacetic acid in an amount of approximately 15 parts by volume; said glycerin in an amount of approximately 73.4 parts by volume; and said water in an amount of approximately 10 parts by volume.

4. A method of making a solution for treating osteoarthritis includes the steps of:

providing magnesium oxide, ethylenediaminetetraacetic acid, glycerin, and water;

heating and stirring said glycerin to a selected temperature;

adding and mixing said ethylenediaminetetraacetic acid to said glycerin for a selected period of time to form a mixture;

increasing heat of said mixture by approximately 45 degrees Fahrenheit;

adding and mixing said magnesium oxide to said mixture for a selected period of time;

cooling said mixture; and adding and mixing water to said mixture until said mixture is consistent and then allowing said mixture to cool before bottling said mixture.

5. A method of making a solution for treating osteoarthritis as described in claim 4, wherein the step of providing magnesium oxide, ethylenediaminetetraacetic acid, glycerin, and water includes the step of providing said magnesium oxide in an amount of approximately 1.6 parts by volume; said ethylenediaminetetraacetic acid in an amount of approximately 15 parts by volume; said glycerin in an amount of approximately 73.4 parts by volume; and said water in an amount of approximately 10 parts by volume.

6. A method of making a solution for treating osteoarthritis as described in claim 5, wherein said step of heating and stirring said glycerin includes the step of heating and stirring said glycerin to a temperature of approximately 140 degrees Fahrenheit.

7. A method of making a solution for treating osteoarthritis as described in claim 4, wherein said step of adding and mixing said ethylenediaminetetraacetic acid to said glycerin includes the step of adding and mixing said ethylenediaminetetraacetic acid to said glycerin for approximately 1 minute.

8. A method of making a solution for treating osteoarthritis as described in claim 4, wherein said step of adding and mixing said magnesium oxide to said mixture includes the step of adding and mixing said magnesium oxide to said mixture for approximately 40 minutes.

9. A method of making a solution for treating osteoarthritis as described in claim 4, wherein said step of cooling said mixture includes the step of cooling said mixture to approximately 140 degrees Fahrenheit.

* * * * *